United States Patent
Maienfisch et al.

(10) Patent No.: US 6,252,072 B1
(45) Date of Patent: Jun. 26, 2001

(54) METHOD FOR PRODUCING NITROGUANIDINE DERIVATIVES

(75) Inventors: Peter Maienfisch, Rodersdorf; Hansjürg Widmer, Basel, both of (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 09/445,608

(22) PCT Filed: Jun. 5, 1998

(86) PCT No.: PCT/EP98/03358

§ 371 Date: Dec. 8, 1999

§ 102(e) Date: Dec. 8, 1999

(87) PCT Pub. No.: WO98/56764

PCT Pub. Date: Dec. 17, 1998

(30) Foreign Application Priority Data

Jun. 9, 1997 (CH) .................................................... 1423/97

(51) Int. Cl.⁷ ..................... C07D 231/04; C07D 251/08; C07D 277/28; C07D 307/14
(52) U.S. Cl. .................... 544/180; 544/215; 546/290; 548/182; 549/492; 564/230
(58) Field of Search .................................. 544/215, 180; 546/290; 548/182; 549/492

(56) References Cited

U.S. PATENT DOCUMENTS 5,245,040    9/1993    Maienfisch et al. ................. 546/275

FOREIGN PATENT DOCUMENTS

0483062  *  10/1991  (EP) .
0649845  *  10/1994  (EP) .
7-173157     7/1995  (JP) .

OTHER PUBLICATIONS

Knapp et al. Amino Protection Using Triazones Tetrahedron Letters vol. 31, No. 15, pp 2109–2112, 1990.
JP 07 173157, Onukuma, Nov. 1995, English Abstract.*
JP 09 227532, Kaiho, Feb. 1997. English Abstract.*

* cited by examiner

Primary Examiner—Richard L. Raymond
Assistant Examiner—Venkataraman Balasubramanian
(74) Attorney, Agent, or Firm—William A. Teoli, Jr.

(57) ABSTRACT

A process for the preparation of compounds of formula

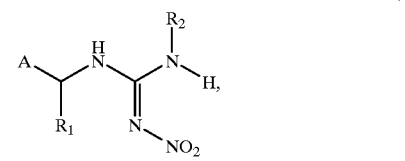

(I)

is described, wherein $R_1$ is hydrogen or $C_1$–$C_4$-alkyl;

$R_2$ is hydrogen, $C_1$–$C_6$-alkyl, $C_3$–$C_6$-cycloalkyl or a radical —$CH_2B$;

A is an unsubstituted or mono- to penta-substituted, aromatic or non-aromatic, monocyclic to bicyclic heterocyclic radical; and B is phenyl, 3-pyridyl or thiazolyl, which are optionally substituted by one to rhee substituents;

by means of the hydrolysis of a compound of formula

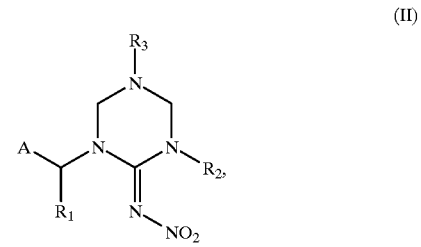

(II)

wherein $R_1$, $R_2$ and A have the same significances as given for formula (I), and $R_3$ signifies unsubstituted or substituted $C_1$–$C_{10}$-alkyl, $C_3$–$C_6$-cycloalkyl, phenyl or benzyl; whereby the reaction is carried out at a pH value of between 7 and 14, as well as starting materials for carrying out the process.

The compounds of formula (I) are suitable as intermediates in the preparation of pesticidal compositions.

5 Claims, No Drawings

METHOD FOR PRODUCING NITROGUANIDINE DERIVATIVES

The invention relates to a process for the preparation of a compound of formula

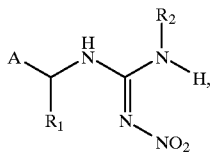

(I)

wherein $R_1$ is hydrogen or $C_1$–$C_4$-alkyl;

$R_2$ is hydrogen, $C_1$–$C_6$-alkyl, $C_3$–$C_6$-cycloalkyl or a radical —$CH_2B$;

A is an aromatic or non-aromatic, monocyclic or bicyclic heterocyclic radical which is unsubstituted or—depending on the substitution possibilities of the ring system—mono- to penta-substituted by substituents selected from the group comprising halogen, $C_1$–$C_3$-alkyl, $C_1$–$C_3$-alkoxy, halogen-$C_1$–$C_3$-alkyl, $C_1$–$_3$-halogenalkoxy, cyclopropyl, halogencyclopropyl, $C_2$–$C_3$-alkenyl, $C_2$–$C_3$-alkynyl, $C_2$–$C_3$-halogenalkenyl and $C_2$–$C_3$-halogenalkynyl, $C_1$–$C_3$-alkylthio, $C_1$–$C_3$-halogenalkylthio, allyloxy, propargyloxy, allylthio, propargylthio, halogenallyloxy, halogenallylthio, cyano and nitro; and B is phenyl, 3-pyridyl or thiazolyl, which are optionally substituted by one to three substituents from the group comprising $C_1$–$C_3$-alkyl, $C_1$–$C_3$-halogenalkyl, cyclopropyl, halogencyclopropyl, $C_2$–$C_3$-alkenyl, $C2$–$C_3$-alkynyl, $C_1$–$C_3$-alkoxy, $C_2$–$C_3$-halogenalkenyl, $C_2$–$C_3$-halogenalkynyl, $C_1$–$C_3$-halogenalkoxy, $C_1$–$C_3$-alkylthio, $C_1$–$C_3$-halogenalkylthio, allyloxy, propargyloxy, allylthio, propargylthio, halogenallyloxy, halogenallylthio, halogen, cyano and nitro; and, if appropriate, the possible E/Z isomers, E/Z isomeric mixtures and/or tautomers thereof, each in free form or in salt form;

by hydrolysis of a compound of formula

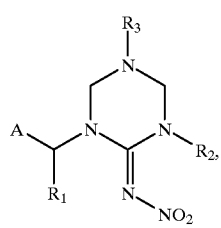

(II)

wherein $R_1$, $R_2$ and A have the same significances as given for formula (I), and $R_3$ signifies unsubstituted or substituted $C_1$–$C_{10}$-alkyl, $C_3$–$C_6$-cycloalkyl, phenyl or benzyl; characterised in that the reaction is carried out at a pH value of between 7 and 14.

The compounds of formula (I) may be present as E/Z isomers, e.g. in the following two isomeric forms

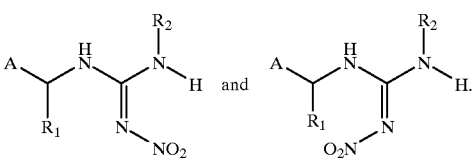

Accordingly, any reference to compounds of formula (I) hereinafter is understood to include also their corresponding E/Z isomers, even if the latter are not specifically mentioned in each case.

The compounds of formula (I) may be present partly in the form of tautomers, for example in the forms

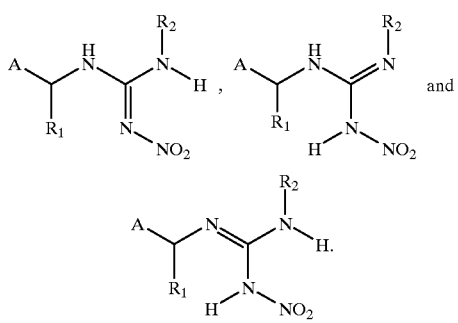

Accordingly, any reference to compounds of formula (I) hereinbefore and hereinafter is understood to include also their corresponding tautomers, even if the latter are not specifically mentioned in each case.

The compounds of formula (I) and, where appropriate, the E/Z isomers and tautomers thereof, may be present as salts. Compounds of formula (I) having at least one basic centre may form e.g. acid addition salts. These are formed for example with strong inorganic acids, typically mineral acids, e.g. sulphuric acid, a phosphoric acid or a hydrohalic acid, or with strong organic carboxylic acids, typically $C_1$–$C_4$alkanecarboxylic acids substituted where appropriate for example by halogen, e.g. acetic acid, such as dicarboxylic acids that are unsaturated where necessary, e.g. oxalic, malonic, maleic, fumaric or phthalic acid, typically hydroxycarboxylic acids, e.g. ascorbic, lactic, malic, tartaric or citric acid, or benzoic acid, or with organic sulphonic acids, typically $C_1$–$C_4$alkane- or arylsulphonic acids substituted where appropriate for example by halogen, e.g. methanesulphonic or p-toluenesulphonic acid. Salt of compounds of formula (I) with acids of the said kind are preferably obtained when working up the reaction mixtures.

In a broader sense, compounds of formula (I) with at least one acid group can form salts with bases. Suitable salts with bases are for example metal salts, typically alkali or alkaline earth metal salts, e.g. sodium, potassium or magnesium salts, or salts with ammonia or an organic amine, such as morpholine, piperidine, pyrrolidine, a mono-, di- or tri-lower alkylamine, e.g. ethyl-, diethyl-, triethyl- or dimethylpropylamine, or a mono-, di- or trihydroxy-lower alkylamine, e.g. mono-, di- or triethanolamine. Corresponding internal salts where appropriate may also be formed. Preferred compounds within the scope of this invention are agrochemically advantageous salts. Hereinbefore and hereinafter, the free compounds of formula (I) and their salts are understood where appropriate to include also by analogy the corresponding salts or free compounds of formula (I). The same applies to E/Z isomers and tautomers of compounds of formula (I) and salts thereof. The free form is preferred.

In the definition of the above formulae (I) and (II), the individual generic terms are to be understood as follows:

The halogen atoms considered as substituents may be both fluorine and chlorine, and bromine and iodine, whereby fluorine, chlorine and bromine are preferred, especially chlorine. Halogen in this context is understood to be an independent substituent or part of a substituent, such as in halogenalkyl, halogenalkylthio, halogenalkoxy, halogencycloalkyl, halogenalkenyl, halogenalkynyl, halogenallyloxy or halogenallylthio. The alkyl, alkylthio, alkenyl, alkynyl and alkoxy radicals considered as substituents may be straight-chained or branched. Examples of such alkyls which may be mentioned are methyl, ethyl, propyl, isopropyl, butyl, isobutyl, sec.-butyl or tert.-butyl. Suitable alkoxy radicals which may be mentioned are, inter alia: methoxy, ethoxy, propoxy, isopropoxy or butoxy and the isomers thereof. Alkylthio is for example methylthio, ethylthio, isopropylthio, propylthio or the isomeric butylthio. If the alkyl, alkoxy, alkenyl, alkynyl or cycloalkyl groups considered as substituents are substituted by halogen, they may be only partially halogenated or also perhalogenated. The above-mentioned definitions apply here to halogen, alkyl and alkoxy. Examples of the alkyl elements of these groups are methyl which is mono- to trisubstituted by fluorine, chlorine and/or bromine, such as $CHF_2$ or $CF_3$; ethyl which is mono- to pentasubstituted by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl, mono- to heptasubstituted by fluorine, chlorine and/or bromine, such as $CH_2CHBrCH_2Br$, $CF_2CHFCF_3$, $CH_2CF_2CF_3$ or $CH(CF_3)_2$; butyl or one of its isomers, mono- to nonasubstituted by fluorine, chlorine and/or bromine, such as $CF(CF_3)CHFCF_3$ or $CH_2(CF_2)_2CF_3$; 2-chlorocyclopropyl or 2,2-difluorocyclopropyl; 2,2-difluorovinyl, 2,2-dichlorovinyl, 2-chloroalkyl, 2,3-dichlorovinyl or 2,3-dibromovinyl.

If the defined alkyl, alkoxy or cycloalkyl groups are substituted by other substituents, they may be mono- or repeatedly substituted by identical or different substituents from those listed. In the substituted groups, it is preferable for one or two further substituents to be present. The cycloalkyl radicals considered as substituents may be, for example, cyclopropyl, cyclobutyl, cyclopentyl or cyclohexyl. Alkenyl and alkynyl groups contain an unsaturated carbon-carbon bond. Typical representatives are allyl, methallyl or propargyl, but also vinyl and ethynyl. The double or triple bonds in allyloxy, propargyloxy, allylthio or propargylthio are separated from the linkage point to the hetero atom (O or S) preferably by a saturated carbon atom.

It is already known that, in order to produce 1,3-disubstituted 2-nitroguanidines, a further substituent may be introduced into monosubstituted 2-nitroguanidines (e.g. by alkylation) (see e.g. EP patent applications 0.375.907, 0.376.279 and 0.383.091). Owing to the presence of three reactive hydrogen atoms in the monosubstituted 2-nitroguanidines used as the starting material in these reactions, the previously proposed substitution reactions of this kind are often non-selective and lead to undesired substitution products. The mentioned EP patent applications describe the production of 1,3-disubstituted 2-nitroguanidines by reacting monosubstituted nitroisothioureas with primary amines whilst cleaving mercaptan. However, these nitroisothiourea compounds, containing alkylthio leaving groups, which are proposed as starting compounds in the known processes, can only be obtained with difficulty.

In addition, EP-A-0.483.062 describes a process for the production of the compounds of formula (I), in which a compound of the above formula (II) is hydrolysed. The examples listed therein show that hydrolysis must be carried out under acidic conditions. In the said patent specification, there are no examples whatsoever regarding the possibility of hydrolysis under basic conditions.

It has now been shown that the above-described processes for the production of compounds of formula (I) do not satisfy the requirements concerning purity and yield, for which reason there is still a need to provide improved processes for the production of these compounds from readily obtainable starting compounds.

It has now surprisingly been found that the process according to the invention is able to satisfy these requirements.

The hydrolysis process according to the invention is preferably carried out at a pH value greater than 7 and up to 12, especially from 8 to 12, particularly 8 to 10, preferably 7 to 10; under normal pressure and at a temperature of 0 to 120° C., preferably 20 to 80° C.

The reaction is carried out in a solvent or diluent that is inert towards the reaction components. Suitable solvents are, in particular, alcohols such as methanol, ethanol, propanol and isopropanol, as well as especially water. Further appropriate solvents are e.g. ethers, such as tetrahydrofuran and dioxane, as well as other solvents which to not adversely affect the reaction. The solvents may also be used as mixtures. A compound of formula (II) is preferably hydrolysed in an aqueous medium or in a mixture of water with an alcohol.

Suitable bases for carrying out the process are preferably hydroxides of alkali metals and alkaline earth metals, such as NaOH and KOH, carbonates such as $Na_2CO_3$, $NaHCO_3$, $K_2CO_3$; phosphates such as $Na_3PO_4$, $Na_2HPO_4$, alcoholates such as sodium methanolate, sodium ethanolate and K-tert.-butanolate, organic amines such as morpholine, piperidine, pyrrolidine, a mono-, di- or tri-lower alkylamine, e.g. ethyl-, diethyl, triethyl- or dimethyl-propyl-amine, or a mono-, di- or trihydroxy lower alkylamine, e.g. mono-, di- or triethanol-amine, or dialkylaniline, for example N,N-dimethyl- or N,N-diethylaniline, as well as salts of organic acids, such as sodium acetate, potassium acetate or sodium benzoate, or mixtures thereof, for example acetate or phosphate buffers.

The process according to the invention is preferably used to produce compounds of formula (I) in which the heterocyclic radical A is unsaturated and is bonded by a carbon atom as a ring member to the fundamental element. Especially preferred radicals A are pyridyl, thiazolyl, tetrahydrofuranyl, dihydrofuranyl, furanyl, N-oxido-pyridinio, oxazolyl, isoxazolyl, thienyl, morpholinyl, piperidinyl, pyridinyl and pyrazinyl; most particularly pyridyl, thiazolyl, tetrahydrofuranyl and N-oxido-pyridinio, especially 3-pyridyl, 2-halogenpyrid-5yl, 2,3-dihalogenpyrid-5-yl, 2-halogenthiazol-5-yl, tetrahydrofuran-3-yl, 5-methyl-tetrahydrofuran-3-yl, 1-oxopyrid-3-yl, 1-oxo2-halogenpyrid-5yl and 1-oxo-2,3-dihalogenpyrid-5-yl.

Equally preferably, the heterocycles A carry one to three substituents from the group halogen, $C_1$–$C_3$-alkyl, $C_1$–$C_3$-halogenalkyl and $C_1$–$C_3$-halogenalkoxy each with 1 to 7 halogen atoms, and $C_1$–$C_3$-alkoxy.

Furthermore, compounds of formula (I) are preferably produced according to the invention, in which the radical B is a phenyl, pyridyl or thiazolyl radical that is unsubstituted or may be substituted by one to two radicals from the group halogen, $C_1$–$C_3$-alkyl, $C_1$–$C_3$-halogenalkyl and $C_1$–$C_3$-halogenalkoxy each with 1 to 7 halogen atoms, and $C_1$–$C_3$-alkoxy.

Of the compounds of formula (I) to be produced according to the invention, those that are notable are those in which $R_1$ is hydrogen, $R_2$ is hydrogen, methyl, ethyl or cyclopropyl and A is pyridyl, 1-oxopyridyl, tetrahydrofuranyl, thiazolyl, or A is pyridyl, 1-oxopyridinio, tetrahydro-furanyl or thiazolyl which is respectively substituted by one to three radicals from the group halogen, $C_1$–$C_3$-alkyl, $C_1$–$C_3$-halogenalkyl and $C_1$–$C_3$-halogenalkoxy each with 1 to 7 halogen atoms, and $C_1$–$C_3$-alkoxy. Also of interest in this context is the preparation of those compounds of formula (I) in which a) $R_1$ is hydrogen;
b) $R_2$ is hydrogen, $C_1$–$C_3$-alkyl or cyclopropyl, especially methyl;
c) A is 2-chloropyrid-5-yl, tetrahydrofuran-3-yl, 5-methyl-tetrahydrofuran-3-yl or 2-chloro-thiazol-5-yl;
d) $R_3$ is $C_1$–$C_3$-alkyl, cyclopropyl, cyclohexyl, phenyl or benzyl.

In formula (II), the substituents which may be considered for the radical $R_3$ are in particular halogen, $C_1$–$C_4$-alkyl, halogen-$C_1$–$C_4$alkyl, nitro, $C_1$–$C_4$-alkoxy and halogen-$C_1$–$C_4$alkoxy.

The compounds of formula (I) which are produced according to the invention are valuable active ingredients in pest control, that are well tolerated by warm-blooded animals, fish and plants. The compounds of formula (I) are especially suitable for the control of insects and arachnids, which appear on crops and ornamentals in agriculture, especially in cotton, vegetable and fruit plantations, in forestry, in the protection of stock and material, as well as in the hygiene sector, especially on domestic animals and productive livestock. The compounds are especially effective against plant-damaging sucking insects, especially against aphids and plant and leaf hoppers. Pesticidally active substituted 2-nitroguanidines of the type that may be produced according to the invention are described e.g. in EP patent applications 376.279, 375.907 and 383.091.

The starting compounds or starting products of formula (II) that may be considered for the process according to the invention are partially known or may be prepared by known processes. If they are new, they similarly form an object of the invention. These are, in particular, the compounds of formula

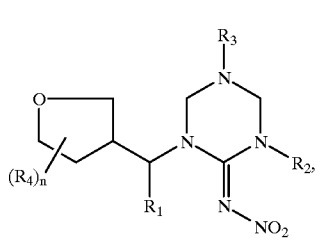

(IIa)

wherein $R_1$, $R_2$, and $R_3$ have the significances given in formula (I).

$R_4$ is halogen, $C_1$–$C_3$-alkyl, $C_1$–$C_3$-alkoxy, halogen-$C_1$–$C_3$-alkyl, $C_1$–$C_3$-halogenalkoxy, cyclopropyl, halogencyclopropyl, $C_2$–$C_3$-alkenyl, $C_2$–$C_3$-alkynyl, $C_2$–$C_3$-halogenalkenyl and $C_2$–$C_3$-halogenalkynyl, $C_1$–$C_3$-alkylthio, $C_1$–$C_3$-halogenalkylthio, allyloxy, propargyloxy, allylthio, propargylthio, halogenallyloxy, halogenallylthio, cyan and nitro, preferably $C_1$–$C_3$-alky n is 0, 1, 2 or 3, preferably 0 or 1;

and, if appropriate, the possible E/Z isomers, E/Z isomeric mixtures and/or tautomers thereof, each in free form or in salt form.

TABLE 1

Compounds of formula

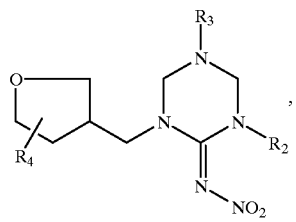

(IIb)

| Comp. no. | $R_4$ | $R_2$ | $R_3$ | phys. data |
|---|---|---|---|---|
| 1.1 | H | H | H | |
| 1.2 | H | H | —$CH_3$ | |
| 1.3 | H | H | —$C_2H_5$ | |
| 1.4 | H | H | cyclopropyl | |
| 1.5 | H | H | benzyl | |
| 1.6 | H | H | 4-Cl-benzyl | |
| 1.7 | H | —$CH_3$ | —$CH_3$ | |
| 1.8 | H | —$C_2H_5$ | —$CH_3$ | |
| 1.9 | H | —$CH_3$ | —$C_2H_5$ | |
| 1.10 | H | —$CH_3$ | cyclopropyl | |
| 1.11 | 5-$CH_3$ | H | H | |
| 1.12 | 5-$CH_3$ | H | —$CH_3$ | |
| 1.13 | 5-$CH_3$ | H | —$C_2H_5$ | |
| 1.14 | 5-$CH_3$ | H | cyclopropyl | |
| 1.15 | 5-$CH_3$ | H | benzyl | |
| 1.16 | 5-$CH_3$ | H | 4-Cl-benzyl | |
| 1.17 | 5-$CH_3$ | —$CH_3$ | —$CH_3$ | |
| 1.18 | 5-$CH_3$ | —$C_2H_5$ | —$CH_3$ | |
| 1.19 | 5-$CH_3$ | —$CH_3$ | —$C_2H_5$ | |
| 1.20 | 5-$CH_3$ | —$CH_3$ | cyclopropyl | |

PREPARATION EXAMPLES

Example 1

Preparation of 1-(2-chloropyrid-5-ylmethyl)-2-nitro-3-methyl-guanidine:

A mixture of 1.5 g of 1-(2-chloropyrid-5-ylmethyl)-2-nitroimino-3-methyl-5-n-propyl-1,3,5-triazacyclohexane, 0.5 g of solid sodium hydrogen carbonate, 20 ml of methanol and 10 ml of water is stirred for 24 hours at 50° C. The reaction mixture is concentrated by evaporation and the residue purified on silica gel with dichloromethane/methanol 95:5 as the eluant. This yields the title compound with a melting point of 149–151° C. (compound 2.2).

Example 2

Preparation of 1-(2-chlorothiazol-5-ylmethyl)-2-nitro-3-methyl-guanidine:

A mixture of 1.5 g of 1-(2-chlorothiazol-5-ylmethyl)-2-nitroimino-3,5-dimethyl-1,3,5-triaza-cyclohexane, 0.3 g of $NaHCO_3$, 20 ml of methanol and 20 ml of water is stirred for 16 hours at 50° C. The reaction mixture is poured onto 100 ml of ethyl acetate and the aqueous phase separated. The organic phase is concentrated by evaporation and the residue purified on silica gel with dichloromethane/methanol 95:5 as the eluant. This yields the title compound with a melting point of 167–169° C. (compound 2.45).

Example 3

Preparation of 1-(2-chloropyrid-5-ylmethyl)-2-nitroguanidine:

A mixture of 1.5 g of 1-(2-chloropyridyl-5-ylmethyl)-2-nitroimino-5-n-propyl-1,3,5-triazacyclo-hexane, 0,77 g of NaHCO$_3$, 20 ml of methanol and 10 ml of water is stirred for 21 hours at 50° C. The reaction mixture is poured onto 100 ml of ethyl acetate, the aqueous phase is separated and the organic phase is washed with water. The organic phase is concentrated by evaporation and the residue purified on silica gel with dichloromethane/methanol 10:1 as the eluant. This yields the title compound with a melting point of 195–197° C. (compound 2.1).

The following compounds of formula (I) listed in Table 2 may also be obtained analogously to the above methods of examples 1 to 3: c-propyl signifies cyclopropyl.

TABLE 2

Compounds of formula (I)

| Comp. no. | A | R$_1$ | R$_2$ | phys. data |
|---|---|---|---|---|
| 2.1 | 2-chloropyrid-5-yl | H | H | m.p. 195–197° C. |
| 2.2 | 2-chloropyrid-5-yl | H | —CH$_3$ | m.p. 149–151° C. |
| 2.3 | 2-chloropyrid-5-yl | H | —C$_2$H$_5$ | m.p. 125–127° C. |
| 2.4 | 2-chloropyrid-5-yl | H | —C$_3$H$_7$(n) | m.p. 122–123° C. |
| 2.5 | 2-chloropyrid-5-yl | H | c-propyl | |
| 2.6 | 2-chloropyrid-5-yl | H | —C$_4$H$_9$(n) | m.p. 88–90° C. |
| 2.7 | 2-chloropyrid-5-yl | H | —CH(CH$_3$)$_2$ | |
| 2.8 | 2-chloropyrid-5-yl | H | benzyl | |
| 2.9 | 2-chloropyrid-5-yl | H | pyrid-3-yl | |
| 2.10 | 2-chloropyrid-5-yl | H | 4-chlorobenzyl | |
| 2.11 | 2-chloropyrid-5-yl | —CH$_3$ | —CH$_3$ | |
| 2.12 | 2-chloropyrid-5-yl | —CH$_3$ | —C$_2$H$_5$ | |
| 2.13 | 2-chloropyrid-5-yl | —CH$_3$ | c-propyl | |
| 2.14 | 2-chloropyrid-5-yl | —CH$_3$ | —C$_3$H$_7$(n) | |
| 2.15 | 2-chloropyrid-5-yl | —C$_2$H$_5$ | —CH$_3$ | |
| 2.16 | 2-chloropyrid-5-yl | —C$_2$H$_5$ | —C$_2$H$_5$ | |
| 2.17 | 2-chloropyrid-5-yl | —C$_2$H$_5$ | c-propyl | |
| 2.18 | 2,3-dichloropyrid-5-yl | H | H | m.p. 207–209° C. |
| 2.19 | 2,3-dichloropyrid-5-yl | H | —CH$_3$ | m.p. 173–175° C. |
| 2.20 | 2,3-dichloropyrid-5-yl | H | —C$_2$H$_5$ | m.p. 159–161° C. |
| 2.21 | 2,3-dichloropyrid-5-yl | H | c-propyl | |
| 2.22 | 2,3-dichloropyrid-5-yl | H | —C$_3$H$_7$(n) | |
| 2.23 | 2,3-dichloropyrid-5-yl | H | —C$_4$H$_9$(n) | m.p. 152–153° C. |
| 2.24 | 2,3-dichloropyrid-5-yl | —CH$_3$ | —CH$_3$ | |
| 2.25 | 2,3-dichloropyrid-5-yl | —CH$_3$ | —C$_2$H$_5$ | |
| 2.26 | 2,3-dichloropyrid-5-yl | —CH$_3$ | c-propyl | |
| 2.27 | 2,3-dichloropyrid-5-yl | —C$_2$H$_5$ | —CH$_3$ | |
| 2.28 | pyridine N-oxide (3-methyl) | H | H | |
| 2.29 | pyridine N-oxide (3-methyl) | H | —CH$_3$ | |
| 2.30 | pyridine N-oxide (3-methyl) | H | —C$_2$H$_5$ | |
| 2.31 | pyridine N-oxide (3-methyl) | H | c-propyl | |
| 2.32 | pyridine N-oxide (3-methyl) | —CH$_3$ | —CH$_3$ | |
| 2.33 | pyridine N-oxide (3-methyl) | —CH$_3$ | —C$_2$H$_5$ | |
| 2.34 | pyridine N-oxide (3-methyl) | —CH$_3$ | c-propyl | |
| 2.35 | 2-chloropyridine N-oxide (5-methyl) | —C$_2$H$_5$ | —CH$_3$ | |
| 2.36 | 2-chloropyridine N-oxide (5-methyl) | H | H | |
| 2.37 | 2-chloropyridine N-oxide (5-methyl) | H | —CH$_3$ | |
| 2.38 | 2-chloropyridine N-oxide (5-methyl) | H | —C$_2$H$_5$ | |
| 2.39 | 2-chloropyridine N-oxide (5-methyl) | H | c-propyl | |
| 2.40 | 2-chloropyridine N-oxide (5-methyl) | —CH$_3$ | —CH$_3$ | |
| 2.41 | 2-chloropyridine N-oxide (5-methyl) | —CH$_3$ | c-propyl | |

TABLE 2-continued

Compounds of formula (I)

| Comp. no. | A | $R_1$ | $R_2$ | phys. data |
|---|---|---|---|---|
| 2.42 | 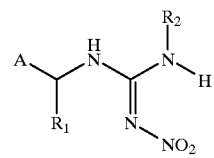 | —CH$_3$ | —C$_2$H$_5$ | |
| 2.43 | 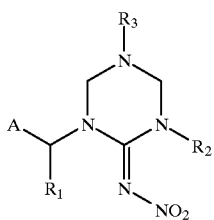 | —C$_2$H$_5$ | —CH$_3$ | |
| 2.44 | 2-chlorothiazol-5-yl | H | H | m.p. 158–160° C. |
| 2.45 | 2-chlorothiazol-5-yl | H | —CH$_3$ | m.p. 167–169° C. |
| 2.46 | 2-chlorothiazol-5-yl | H | —C$_2$H$_5$ | m.p. 135–136° C. |
| 2.47 | 2-chlorothiazol-5-yl | H | c-propyl | |
| 2.48 | 2-chlorothiazol-5-yl | H | benzyl | |
| 2.49 | 2-chlorothiazol-5-yl | H | 4-Cl-benzyl | |
| 2.50 | 2-chlorothiazol-5-yl | —CH$_3$ | —CH$_3$ | |
| 2.51 | 2-chlorothiazol-5-yl | —C$_2$H$_5$ | —CH$_3$ | |
| 2.52 | 2-chlorothiazol-5-yl | —CH$_3$ | —C$_2$H$_5$ | |
| 2.53 | 2-chlorothiazol-5-yl | —CH$_3$ | c-propyl | |
| 2.54 | tetrahydrofuran-3-yl | H | H | |
| 2.55 | tetrahydrofuran-3-yl | H | —CH$_3$ | |
| 2.56 | tetrahydrofuran-3-yl | H | —C$_2$H$_5$ | |
| 2.57 | tetrahydrofuran-3-yl | H | c-propyl | |
| 2.58 | tetrahydrofuran-3-yl | H | benzyl | |
| 2.59 | tetrahydrofuran-3-yl | H | 4-Cl-benzyl | |
| 2.60 | tetrahydrofuran-3-yl | —CH$_3$ | —CH$_3$ | |
| 2.61 | tetrahydrofuran-3-yl | —C$_2$H$_5$ | —CH$_3$ | |
| 2.62 | tetrahydrofuran-3-yl | —CH$_3$ | —C$_2$H$_5$ | |
| 2.63 | tetrahydrofuran-3-yl | —CH$_3$ | c-propyl | |
| 2.64 | 5-methyl-tetrahydrofuran-3-yl | H | H | |
| 2.65 | 5-methyl-tetrahydrofuran-3-yl | H | —CH$_3$ | |
| 2.66 | 5-methyl-tetrahydrofuran-3-yl | H | —C$_2$H$_5$ | |
| 2.67 | 5-methyl-tetrahydrofuran-3-yl | H | c-propyl | |
| 2.68 | 5-methyl-tetrahydrofuran-3-yl | H | benzyl | |
| 2.69 | 5-methyl-tetrahydrofuran-3-yl | H | 4-Cl-benzyl | |
| 2.70 | 5-methyl-tetrahydrofuran-3-yl | —CH$_3$ | —CH$_3$ | |
| 2.71 | 5-methyl-tetrahydrofuran-3-yl | —C$_2$H$_5$ | —CH$_3$ | |
| 2.72 | 5-methyl-tetrahydrofuran-3-yl | —CH$_3$ | —C$_2$H$_5$ | |
| 2.73 | 5-methyl-tetrahydrofuran-3-yl | —CH$_3$ | c-propyl | |

What we claim is:

1. A process for the preparation of a compound of formula I $$\text{(I)}$$

wherein $R_1$ is selected from the group consisting of hydrogen and $C_1$–$C_4$alkyl;

$R_2$ is selected from the group consisting of hydrogen, $C_1$–$C_3$alkyl, and cyclopropyl;

A is selected from the group consisting of 2-chloropyrid-5-yl, tetrahydrofuran-3-yl, 5-methyl-tetraqhydrofuran-3-yl, and chlorothiazolyl;

by hydrolysis of a compound of formula II $$\text{(II)}$$

wherein $R_1$, $R_2$, and A have the same meanings as above in formula (I), and $R_3$ is selected from the group consisting of $C_1$–$C_3$alkyl, cyclopropyl, cyclohexyl, phenyl, and benzyl;

wherein said hydrolysis is carried out at a pH of between 7 and 14.

2. The process of claim 1 wherein said compound of formula I is produced in the form of a free base.

3. The process of claim 1 wherein $R_1$, is hydrogen.

4. The process of claim 1 wherein said hydrolysis reaction is carried out at a pH of from greater than 7 up to 12.

5. The process of claim 1 wherein said hydrolysis reaction is carried outin water, an alcohol, or a mixture of water and alcohol.

* * * * *